United States Patent
Castellana

(10) Patent No.: US 9,192,634 B2
(45) Date of Patent: Nov. 24, 2015

(54) PROBIOTIC COMPOSITION FOR ORAL HEALTH

(71) Applicant: Jordi Cũńe Castellana, Bellaterra (ES)

(72) Inventor: Jordi Cũńe Castellana, Bellaterra (ES)

(73) Assignee: AB-Biotics S.A., Cerdanyola (ES)

(*) Notice: Subject to any disclaimer, the term of this patent is extended or adjusted under 35 U.S.C. 154(b) by 0 days.

(21) Appl. No.: 14/703,949

(22) Filed: May 5, 2015

(65) Prior Publication Data

US 2015/0273000 A1    Oct. 1, 2015

Related U.S. Application Data

(62) Division of application No. 13/817,378, filed as application No. PCT/EP2011/064173 on Aug. 17, 2011.

(30) Foreign Application Priority Data

Aug. 18, 2010 (EP) .................................. 10173286

(51) Int. Cl.
- *A01N 63/00* (2006.01)
- *A61K 35/747* (2015.01)
- *A61K 8/99* (2006.01)
- *A61Q 11/00* (2006.01)

(52) U.S. Cl.
CPC .................. *A61K 35/747* (2013.01); *A61K 8/99* (2013.01); *A61Q 11/00* (2013.01)

(58) Field of Classification Search
None
See application file for complete search history.

(56) References Cited

FOREIGN PATENT DOCUMENTS

| FR | 2 448 865 | 9/1980 |
|---|---|---|
| KR | 10-0780030 | 11/2007 |
| KR | 10-0866504 | 10/2008 |
| WO | WO 02/18542 | 3/2002 |
| WO | WO 02/39825 | 5/2002 |
| WO | WO 2005/082157 | 9/2005 |
| WO | WO 2006/080035 | 8/2006 |

OTHER PUBLICATIONS

International Search Report from the European Patent Office for International Application No. PCT/EP2011/064173, mailed Sep. 12, 2011.
Twetman, L. et al., "Coaggregation Between Probiotic Bacteria and Caries-Associated Strains: An in virto Study," Acta Odontologica Scandinavica, vol. 67. pp. 284-288, (2009).
Della Riccia, D.N. et al., "Anti-Inflammatory Effects of Lactobacillus brevis (CD2) on Periodontal Disease," Oral Diseases, vol. 13, pp. 376-385, (2007).
Smith, S. I, et al., "Lectobacilli in Human Dental Caries and Saliva," Microbios, vol. 105, pp. 77-85, (2001).
Rodis, O. M. M. et al., "Culture-Based PCR Analysis of Plaque Samples of Japanese School Children to Assess the Presence of Six Common Carlogenic Bacteria and Its Association with Caries Risk," Molecular and Cellular Probes, vol. 23, pp. 259-263, (2009).
Yang, Y. et al., "Probiotic Characteristics of Lactobacillus Plantarum HO-69 applied in Oral Cavity," China Journai of Stomatology, vol. 26, pp. 482-485, 489, (2008).
Wang, Q. et al., "Naive Bayeslan Classifier for Rapid Assignment of rRNA Sequences into the New Bacterial Taxonomy", Applied and Environmental Microbiology, vol. 73, No. 16, pp. 5261-5267, (2007).
Twetman, S. et al., "Short-Term Effect of Chewing Gums Containing Probiotic Lactobacillus Reuteri on the Levels of Inflammatory Mediators in Gingival Crevicular Fluid," Acta Odontologica Scandinavics, vol. 67, pp. 19-24, (2009).
Bories, G. et al., "Technical Guidance Update of the Criteria Used in the Assessment of Bacterial Resistance to Antibiotics of Human or Veterinary Importance," The EFSA Journal, vol. 732, pp. 1-15, (2008).
Rodas, A. M. et al., "Polyphasic study of Wine Lactobacillus Strains: Taxonomic Implications," International Journal of Systematic and Evolutional Microbiology vol. 55, pp. 197-207, (2005).
Caglar, E. et al., "Salivary Mutens Streptococci and Lactobacilli Leveis After Ingestion of the Probiotic Bacterium Lactobacillus Reuteri ATCC 55730 by Straws or Tablets," Acta Odontologica Scandlnavica, vol. 64, pp. 314-318, (2006).
Stamatova, I. et al., "In Vitro Evaluation of Yoghurt Starter Lactobacilli and Lactobacillus Rhamnosus GG Adhesion to Saliva-Coated Surfaces," Oral Microbiology Immunology, vol. 24, pp. 218-223. (2009).
Cole, J. R. et al., "The Ribosomal Database Project (RDP-II); Introducing myRDP Space and Quality Controlled Public Data," Nucleic Acids Research, vol. 35, pp. D169-D172. (2007).
Burton, J. P. et al., "A Preliminary Study of the Effect of Probiotic Streptococcus Salivarius K12 on Oral Malodour Parameters," Journal of Applied Microbiology, vol. 100, pp.754-764, (2006).

*Primary Examiner* — Blaine Lankford
*Assistant Examiner* — Thomas J Visone
(74) *Attorney, Agent, or Firm* — Finnegan, Henderson, Farabow, Garrett & Dunner LLP

(57) ABSTRACT

The present invention provides a composition comprising an effective amount of *Lactobacillus plantarum* CECT 7481 and *Lactobacillus brevis* CECT 7480. Said strains exhibit various functional properties that make them suitable for their use in the improvement of oral health. Such properties include not only good antagonistic properties against oral pathogens, but also the ability to colonize the oral cavity and a low acidification profile. The invention also provides for the use of said composition as a probiotic and/or a medicament for oral health applications as well as products containing said composition.

17 Claims, 1 Drawing Sheet

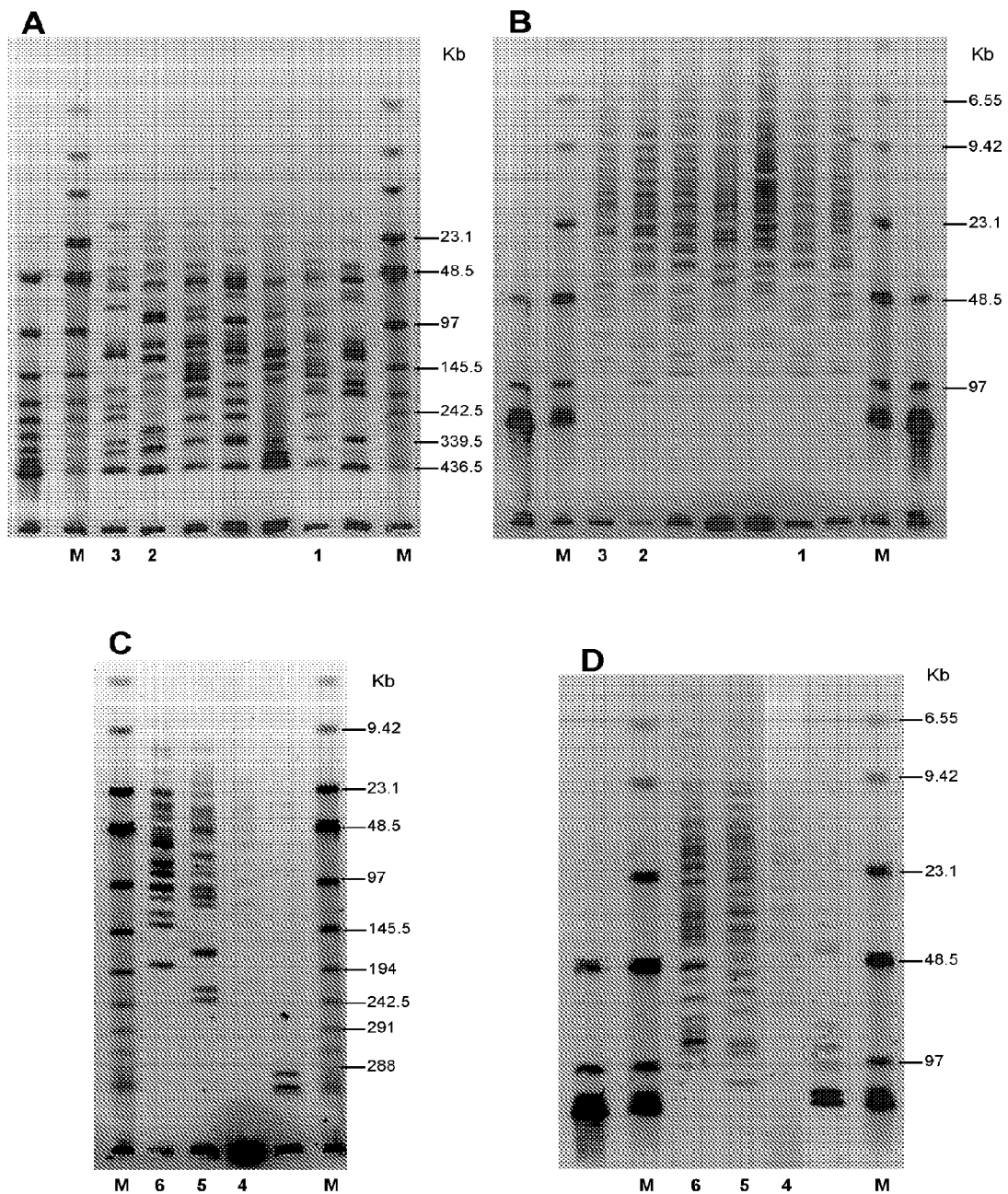

SEQUENCE LISTING

```
<160> NUMBER OF SEQ ID NOS: 6

<210> SEQ ID NO 1
<211> LENGTH: 19
<212> TYPE: DNA
<213> ORGANISM: artificial sequence
<220> FEATURE:
<223> OTHER INFORMATION: forward Eub27f primer

<400> SEQUENCE: 1
gagtttgatc ctggctcag                                                19

<210> SEQ ID NO 2
<211> LENGTH: 22
<212> TYPE: DNA
<213> ORGANISM: Artificial Sequence
<220> FEATURE:
<223> OTHER INFORMATION: reverse Eub1492r primer
```

```
<400> SEQUENCE: 2
tacggytacc ttgttacgac tt                                                    22

<210> SEQ ID NO 3
<211> LENGTH: 20
<212> TYPE: DNA
<213> ORGANISM: Artificial Sequence
<220> FEATURE:
<223> OTHER INFORMATION: forward 27f primer

<400> SEQUENCE: 3
agagtttgat cctggctcag                                                       20

<210> SEQ ID NO 4
<211> LENGTH: 57
<212> TYPE: DNA
<213> ORGANISM: Artificial Sequence
<220> FEATURE:
<223> OTHER INFORMATION: forward 357f primer

<400> SEQUENCE: 4
cgcccgccgc gccccgcgcc cggcccgccg ccccgcccc cctacgggag gcagcag        57

<210> SEQ ID NO 5
<211> LENGTH: 20
<212> TYPE: DNA
<213> ORGANISM: Artificial Sequence
<220> FEATURE:
<223> OTHER INFORMATION: reverse 907r primer

<400> SEQUENCE: 5
ccgtcaattc ctttgagttt                                                       20

<210> SEQ ID NO 6
<211> LENGTH: 19
<212> TYPE: DNA
<213> ORGANISM: Artificial Sequence
<220> FEATURE:
<223> OTHER INFORMATION: reverse 1492r primer

<400> SEQUENCE: 6
ggttaccttg ttacgactt                                                        19
```

PROBIOTIC COMPOSITION FOR ORAL HEALTH

RELATED APPLICATION INFORMATION

This is a division of application Ser. No. 13/817,378, filed Feb. 15, 2013 (35 U.S.C. §371 date Mar. 27, 2013), which is a national stage filing of International Application No. PCT/EP2011/064173, filed on Aug. 17, 2011, which claims the benefit of European Patent Application No. EP 10173286.5, filed on Aug. 18, 2010, all of which are incorporated herein by reference.

REFERENCE TO SEQUENCE LISTING

An electronic copy of the sequence listing was submitted in International Application No. PCT/EP2011/064173 on Feb. 23, 2012. That sequence listing is part of the specification and is incorporated herein by reference in its entirety.
Probiotic Composition for Oral Health The present invention relates to the fields of medicine, microbiology and nutrition and, particularly, to a novel combination of probiotic *Lactobacillus* strains and compositions useful in the field of oral health.

BACKGROUND ART

Dental plaque-related diseases, particularly gingivitis, periodontitis and caries, represent a major part of the global burden of oral diseases.

Periodontal diseases (gingivitis and periodontitis) are largely caused by specific gram-negative anaerobic bacterial infections, leading to the initial destruction of the soft connective tissue and, subsequently, to the disruption of the underlying alveolar bone and ligament supporting the teeth. The bacterial species *Porphyromonas gingivalis* has been implicated as a major etiologic agent in the development and progression of periodontitis. Other species also contributing to gingival inflammation are *Treponema denticola, Prevotella denticola* and *Fusobacterium nucleatum*. Based on the World Health Organization surveys, most children have signs of gingivitis, and among adults the initial stages of periodontal disease are highly prevalent. For example, in Europe, an estimated 15-35% of the adult population suffers from this multifactorial disease.

Dental caries (also known as tooth decay) is a disease wherein bacterial processes damage hard tooth structure. *Steptococcus mutans* is one of a few specialized organisms equipped with receptors that help for better adhesion to the surface of teeth, thus being an early coloniser of the dental surface and the most significant contributor to caries. The growth and metabolism of this pioneer species creates an acidic environment in the mouth which causes the highly mineralized tooth enamel to be vulnerable to decay.

In addition to the above, one further oral disorder is believed to affect a large proportion of the population: halitosis. Also referred to as bad breath, halitosis is caused by a number of volatile compounds which are derived from the bacterial degradation of sulphur-containing amino acids. The implicated bacteria (mostly *Fusobacterium nucleatum, Porphyromonas gingivalis, Porphyromonas intermedia*, and *Treponema denticola*) are located in stagnant areas in the oral cavity, such as the dorsal surface of tongue, periodontal pockets, and interproximal areas. This affection has a significant impact—personally and socially—on those who suffer from it, and is estimated to be the third-most-frequent reason for seeking dental aid, following tooth decay and periodontal disease.

Oral bacteria form a biofilm (dental plaque) on all hard and soft oral tissues which is considered to be the principal etiologic agent in the pathological conditions of the mouth. The accumulation of bacteria within the biofilm, facilitated by poor oral health maintenance, predisposes to allogenic shifts in the microbial community, leading to the onset of periodontal inflammation and caries formation, as well as contributing to halitosis.

Yeasts, and particularly, *Candida albicans*, may also be the cause of disorders in the oral cavity. The elderly are vulnerable to *Candida* infection provoked by chronic diseases, medication, poor oral hygiene, reduced salivary flow, or the impairment of the immune system. Even though the colonization by *Candida* may be asymptomatic, heavy growth usually leads to local candidiasis, with various types of mucosal lesions and symptoms.

Modifying the pathogenic potential of the microbiota within the oral cavity would be an interesting strategy in combating these disorders. On this direction, the introduction of probiotic lactobacilli to partially replace pathogenic microorganisms is a promising means for controlling oral infections. However, as compared with gastrointestinal affections, the use of probiotics for oral health applications has been scarcely studied. At present, very few commercial products containing probiotics are being marketed which incorporate such a health applications.

One of these products is Prodentis® from BioGaia. Prodentis is a chewing gum that contains a probiotic *L. reuteri* ATCC 55730 strain and has demonstrated to reduce gingivitis in a clinical trial (Twetman S, et al. "Short-term effect of chewing gums containing probiotic *Lactobacillus_ reuteri* on the levels of inflammatory mediators in gingival crevicular fluid". *Acta Odontol Scand*, 2009, vol. 67, p. 19-24). This same strain, *L. reuteri* ATCC 55730, has been reported to exert a strong antagonistic activity against cariogenic *Streptococcus mutans* (Caglar E, et al. "Salivary *mutans* streptococci and lactobacilli levels after ingestion of the probiotic bacterium *Lactobacillus_reuteri* ATCC 55730 by straws or tablets". *Acta Odontol Scand*, 2009, vol. 64, p. 314-318). However, little is known about the impact of *L. reuteri* ATCC 55730 on other oral pathogens. Further, *L. reuteri* has been isolated from the intestine, not from the oral cavity, and it is not known whether this strain has the ability to form biofilms or otherwise colonise this environment in order to have a long-lasting effect. It has been shown that *Lactobacillus* sp. vary greatly in their adherent capacity to saliva-coated surfaces in a test model system mimicking oral cavity conditions (Stamatova I, et al. "In vitro evaluation of yoghurt starter lactobacilli and *Lactobacillus rhamnosus* GG adhesion to saliva-coated surfaces". *Oral Microbiol Immunol*, 2009, vol. 24, p. 218-223).

*Streptococcus salivarius* K12 is another commercial probiotic intended for use in the oral cavity. *S. salivarius* K12 was isolated from the saliva of a healthy child and has been shown to perform in vitro antimicrobial activity against various bacterial species incriminated in the etiology of halitosis (Burton J P, et al. "Preliminary study of the effect of probiotic *Streptococcus salivarius* K12 on oral malodor parameters". *J Appl Microbiol*, 2006, vol. 100, p. 754-764). However, the beneficial effects of this strain are limited to the amelioration of halitosis symptoms.

Probiotics have therefore a potentiality to provide beneficial effects in the oral cavity, provided that suitable probiotic strains are identified. In this attempt, it is necessary to consider the putative benefits for the host, but also the safety of the strain, as well as possible adverse effects in the oral cavity. The latter acquires special relevance while contemplating the use of oral lactobacilli, since certain oral lactobacilli have been described as cariogenic due to their high acidogenic potential which favours the degradation of hard tissues, such as enamel and dentine.

Despite the advances in the field of oral probiotics, it is clear from the above that new probiotic strains are needed which, having a wide spectrum of benefits in the oral cavity, do not present adverse effects.

SUMMARY OF THE INVENTION

The inventors have isolated new strains from the human oral microbiota. This strains, *Lactobacillus plantarum* CECT 7481 and *Lactobacillus brevis* CECT 7480, exhibit various functional properties that makes them suitable for their use in the improvement of oral health. Such properties include not only good antagonistic properties against oral pathogens, but also the ability to colonise the oral cavity and a low acidification profile. As discussed below, it has also been found that, when both strains are used in a single combination, the health benefits in the oral cavity are remarkable.

Thus, in a first aspect the present invention provides a composition comprising *Lactobacillus plantarum* CECT 7481 and *Lactobacillus brevis* CECT 7480.

It is clear that by using the deposited strains as starting material, the skilled person in the art can routinely, by conventional mutagenesis or re-isolation techniques, obtain further mutants or derivatives thereof that retain or enhance the herein described relevant features and advantages of the strains forming the composition of the invention. Such mutants or derivatives may be genetically modified or naturally occurring. The skilled person in the art will decide upon the adequate method to be employed for determining the functional activities of the strains. Examples of possible methods to measure these activities are shown in the examples below.

Thus, by "*Lactobacillus plantarum* CECT 7481" it is understood the *Lactobacillus plantarum* strain deposited in the Spanish Type Culture Collection under the accession number CECT 7481, as well as mutant or derivative microorganisms that have been obtained by techniques known in the state of the art using the deposited strain as starting material, such mutants or derivatives at least retaining the herein described relevant features and advantages of the strain *Lactobacillus plantarum* CECT 7481. By "*Lactobacillus brevis* CECT 7480" it is understood the *Lactobacillus brevis* strain deposited in the Spanish Type Culture Collection under the accession number CECT 7480, as well as mutant or derivative microorganisms that have been obtained by techniques known in the state of the art using the deposited strain as starting material, such mutants or derivatives at least retaining the herein described relevant features and advantages of the strain *Lactobacillus brevis* CECT 7480.

The strains of the present invention have the advantage that they are particularly useful as probiotics.

The term "probiotic" is recognised in the state of the art as a microorganism which, when administered in adequate amounts, confers a health benefit to the host. A probiotic microorganism must fulfil several requirements related to lack of toxicity, viability, adhesion and beneficial effects. These probiotic features are strain-dependent, even among bacteria of the same species. Therefore, it is important to find those strains that have a better performance in all probiotic requirements.

Preferably, the strains of the invention are useful as oral probiotics, i.e. probiotics for enhancing oral health. It has been found that *Lactobacillus plantarum* CECT 7481 and *Lactobacillus brevis* CECT 7480 display a significant inhibitory activity against a broad number of pathogens of the oral cavity that are implicated in the development of oral disorders, such as gingivitis, periodontitis, caries and halitosis, while displaying minimal antagonism against common commensal strains of the human oral flora. Moreover, these two strains show a lack of inhibitory activity between them, thus allowing their combined use in a single formula. Furthermore, as can be seen in the examples below, the combination of these strains into a single formula (i.e. the composition of the invention) has the advantage of displaying a higher antagonistic activity against oral pathogens as compared to the activity of the individual strains used separately. Thus, the strains of the invention display a cooperative activity against oral pathogens and are especially useful when used in combination.

By antagonising microorganisms that are implicated in pathological conditions in the oral cavity, such as *Streptococcus mutans, Porphyromonas gingivalis, Treponema denticola, Prevotella denticola* and *Fusobacterium nucleatum*, these strains have the effect of altering the oral microbiological profile to a healthier profile, thereby benefiting oral health conditions.

However, the sole ability of a bacterial strain to antagonise oral pathogens does not suffice to ensure a probiotic effect in the oral cavity. The strains of the composition of the invention are good oral probiotics since, in addition to a strong antagonistic activity, they exhibit a good ability to colonise the oral cavity. As can be seen in example 7 below, *Lactobacillus plantarum* CECT 7481 and *Lactobacillus brevis* CECT 7480 are able to grow in the presence of lysozyme and hydrogen peroxide. Advantageously, these strains also have a good ability to adhere to oral tissues.

Furthermore, the strains of the invention have the advantage of displaying a high ability to form aggregates. This is important because it enables said strains to inhibit or reduce dental plaque by interfering with pathogens biofilm formation. It is known that lactic acid bacteria probiotic strains with aggregation activity can inhibit or reduce dental plaque formation by pathogenic bacteria, which is the result of the aggregation of pathologic bacteria among each other and also with other microorganisms. As mentioned above, the biofilm formed by oral pathogens on hard and soft oral tissues is considered to be an important etiologic agent in the pathological conditions of the mouth, leading to the onset of periodontal inflammation, caries formation and halitosis. The formation of aggregates by the strains of the invention is increased when both strains are combined into a composition, meaning that the strains are more effective in displacing pathogenic bacteria when combined into a single formula.

Surprisingly, the inventors also found that strains CECT 7481 and CECT 7480 display a particularly low acidification profile. *Lactobacillus* species, like most lactic acid bacteria, are characterised by a high production of volatile acids as a result of fermentation of sugars in the human diet. However, the acidogenic property of these bacteria can be a possible side-effect in the oral cavity, since it raises the risk of caries. Indeed, many lactobacilli have been considered as being cariogenic. Therefore, the reduced acid production displayed by the *Lactobacillus* strains forming the composition of the invention renders them particularly suitable for health applications in the oral cavity.

On top of the beneficial properties commented above, the strains of the invention have the advantage of producing none or very low quantities of malodor compounds, such as volatile sulphur compounds, valeric acid, butyric acid and putrescina. This is also of relevance when applying the composition of the invention in the oral cavity.

Additionally, as corresponds to strains for use as probiotics, the strains forming the composition of the invention belong to a bacterial species that has the "Qualified Presumption of Safety" (QPS) status, as defined by the European Food Safety Authority (EFSA). Further, the inventors have found that these strains do not display any significant resistance to antibiotics of human and/or veterinary importance (ampicillin, gentamicin, streptomycin, erythromycin, tetracycline, clindamycin, and chloramphenicol), thus precluding the risk of a potential transfer of antibiotic resistance to pathogenic species.

Considering the above, the strains of the invention have a better performance for all parameters relevant for an oral probiotic when compared with commercial strains which are known in the art oral probiotics. As shown in the examples bellow, the new strains are more resistant to oral conditions, have greater ability to form aggregates, higher (and wider) antagonistic activity, better adhesion and/or lower acidification profile than *Streptococcus salivarius* K12 and *Lactobacillus reuteri* ATTC 55730 and *Lactobacillus brevis* CD2. Protocols for determining each one of said properties are included below. Additionally, the combination of both strains of the invention into a single composition generally results in a cooperative performance of the strains in relevant functionalities. Thus a composition comprising both strains is particularly appropriate for use as an oral probiotic.

In exerting several beneficial effects in the human host, the composition of the first aspect of the invention is useful as medicament. Particularly, when the composition comprising *Lactobacillus plantarum* CECT 7481 and *Lactobacillus brevis* CECT 7480 is administered, it is useful in the prevention and/or treatment of disorders in the oral cavity and, preferably, for the prevention and/or treatment of disorders caused by pathogens in the oral cavity.

Without wishing to be bound by theory, the beneficial effect of the strains forming the composition of the invention is the result of improving the microbiological profile of the oral cavity to yield a healthier oral flora. Growth in the oral cavity of these beneficial bacteria induces an environmental pressure that inhibits the growth of common and/or opportunistic pathogenic microorganisms. This environmental pressure is derived from the competition for adhesion sites and nutrients, the production of antimicrobial compounds and the displacement of pathogens by aggregation of the probiotic bacteria.

One further item to take into consideration is the ability of probiotic bacteria to modulate the immune response. The mechanisms by which probiotics modulate immunity have been broadly studied on gastrointestinal structures. Probiotic species have shown their ability to alter the balance of pro-inflammatory and anti-inflammatory cytokines secreted by epithelial cells. Probiotics also regulate immune responses by enhancing innate immunity and modulating pathogen-induced inflammation via toll-like receptor-regulated signalling pathways. The enhancement of local immune responses, as well as of systemic immune responses by probiotics can offer new opportunities for probiotics in preventing infections at peripheral mucosal surfaces, such as those in the oral cavity.

Accordingly, in a third aspect, the invention provides a composition comprising the strains of this invention for use as a medicament.

In a fourth aspect, the invention provides the composition as defined in the first aspect of the invention for use in the prevention and/or treatment of a disorder from the oral cavity that is caused by oral pathogens in an animal, including a human. Alternatively, this aspect can be formulated as the use of the composition as defined in the first aspect of the invention for the manufacture of a medicament for the prevention and/or treatment of a disorder from the oral cavity that is caused by oral pathogens in an animal, including a human.

The invention also provides a method for the prevention and/or treatment of a disorder from the oral cavity that is caused by oral pathogens in an animal, including a human, comprising administering to said animal in need thereof the composition as defined in the first aspect of the invention.

The term "disorder from the oral cavity which is caused by oral pathogens" is used herein in its broadest meaning as any derangement or abnormality that can be found in the oral cavity which has been caused by an oral pathogen such as bacteria, viruses or yeasts. Such disorder can be a serious pathological condition as well as a trivial condition or discomfort. Illustrative non-limitative examples of "disorder from the oral cavity which is caused by an oral pathogen" are caries, gingivitis, periodontitis, candidiasis, herpes and ulcers, as well as halitosis, stained teeth, sensitive teeth, among others.

In one embodiment of the fourth aspect of the invention the composition is used for the treatment and/or prevention of a dental plaque related disorder. Preferably, the dental plaque related disorder is selected from the group consisting of caries, sensitive teeth, gingivitis and periodontitis.

In another embodiment of the fourth aspect of the invention the composition is used for the treatment and/or prevention of halitosis.

In a further embodiment of the fourth aspect of the invention the composition is used for the treatment and/or prevention of candidiasis.

The composition according to the invention that comprises the strains of the invention can be formulated as edible, cosmetical or pharmaceutical products. Said composition can comprise, in addition to the strains of the invention, one or more other active agents and/or cosmetically acceptable excipients (in the case of a cosmetical composition), pharmaceutically acceptable excipients (in the case of a pharmaceutical composition) or adequate edible ingredients (in the case of an edible composition). In a particular embodiment of the invention, the composition of the invention further comprises one or more active agents. Preferably, the additional active agent or agents are other probiotic bacteria which are not antagonic to the strains forming the composition of the invention. More preferably, the additional active agent or agents are suitable for treating and/or preventing halitosis, candidiasis, caries, sensitive teeth and/or periodontal diseases. Depending on the formulation, the strains may be added as purified bacteria, as a bacterial culture, as part of a bacterial culture, as a bacterial culture which has been post-treated, and alone or together with suitable carriers or ingredients. Prebiotics could be also added.

The composition may be in solid, liquid or gaseous form and may be, inter alia, in the form of powders, tablets, film preparations, solutions, aerosols, granules, lozenges, pills, suspensions, emulsions, capsules, syrups, liquids, elixirs, extracts, tincture or fluid extracts or in a form which is particularly suitable for oral administration.

In other aspects the invention provides a pharmaceutical composition that contains the composition of the invention together with pharmaceutically acceptable excipients. In this regard, the pharmaceutical product may be prepared in any suitable form which does not negatively affect the bioavailability of the strains forming the composition of the invention. Selection of the excipients and the most appropriate methods for formulation in view of the particular purpose of the composition is within the scope of the person skilled in the art of pharmaceutical technology.

The term "pharmaceutically acceptable" as used herein refers to compounds, materials, compositions, and/or dosage forms which are, within the scope of sound medical judgement, suitable for use in contact with the tissues of a subject (either a human or non-human animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

Another aspect of the invention provides a cosmetical composition that contains the composition of the invention together with cosmetically acceptable excipients. In preventing and/or treating oral disorders caused by pathologic bacteria, the composition of the invention is useful for the amelioration and/or prevention of the symptoms produced by these disorders. Such symptoms include, but are not limited to, bad breath and stained teeth.

The term "cosmetically acceptable" refers to compounds, materials, compositions, and/or dosage forms which are, within the scope of sound medical judgement, suitable for use in contact with human skin without undue toxicity, incompatibility, instability and allergic response, among others. Each "cosmetically acceptable" carrier, excipient, etc., must also be "acceptable" in the sense of being compatible with the other ingredients of the cosmetic formulation. Suitable carriers, excipients, etc. for cosmetic formulations can be found in standard texts.

The strains of the invention can be also included in a variety of edible products, such as milk products, yogurt, curd, cheese (e.g. quark, cream, processed, soft and hard), fermented milk, milk powder, milk based fermented product, ice-cream, a fermented cereal based product, milk based powder, a beverage, a dressing, and a pet food. The term "edible product" is used herein in its broadest meaning, including any type of product, in any form of presentation, which can be ingested by an animal, but excluding cosmetical, pharmaceutical and veterinary products. Examples of other edible products are meat products (e.g. liver paste, frankfurter and salami sausages or meat spreads), chocolate spreads, fillings (e.g. truffle, cream) and frostings, chocolate, confectionery (e.g. caramel, candy, fondants or toffee), baked goods (cakes, pastries), sauces and soups, fruit juices and coffee whiteners. Fodders for animal food are also included in the scope of the invention. The compositions of the invention could be also used as an ingredient in other food products. Particularly interesting edible products are functional foods and infant formulas.

Accordingly, in another aspect of the invention, an edible composition is provided which contains the composition of the invention together with other edible ingredients.

The term "edible ingredients" refers to ingredients which are fit to be eaten, i.e. to be used as food, by an animal, preferably but not limited to humans, cattle or pet animals.

Often, probiotic bacterial compositions such as the one disclosed herein, are considered as dietary supplements. Dietary supplements, also known as food supplements or nutritional supplements, provide beneficial ingredients that are not usually ingested in the normal diet. Mostly, dietary supplements are considered as food products, but sometimes they are defined as drugs, natural health products, or nutraceutical products. In the sense of the present invention, dietary supplements also include nutraceuticals. Dietary supplements are usually sold "over the counter", i.e. without prescription. In a preferred embodiment, the composition of the invention is a dietary supplement.

If the composition according to the invention is a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, lozenges, granules, powders, suspensions, sachets, pastilles, sweets, bars, syrups and corresponding administration forms, usually in the form of a unit dose. Preferably, the dietary supplement comprising the composition of the invention is administered in the form of tablets, lozenges, capsules or powders, manufactured in conventional processes of preparing dietary supplements.

As can be derived from the above, the products comprising the composition of the invention are meant for use in oral health applications, either by preventing or treating an oral disorder, or by ameliorating the symptoms derived from these disorders. Accordingly, another aspect of the present invention provides an oral care product comprising the composition as mentioned above, together with pharmaceutically excipients, or cosmetically acceptable excipients, or other edible ingredients.

In the sense of the present invention, it may well be that the composition is an oral product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. Non limiting examples of such products are toothpastes, dentifrices, tooth powders, topical oral gels, mouth rinses, denture products, mouth sprays, chewing gums, dental floss or dental tapes. The oral composition may be a single phase oral composition or may be a combination of two or more oral compositions.

In one embodiment, the oral care product is a chewing gum, a tooth-paste, a mouth spray, a lozenge or an oral dispersible tablet. Preferably, the oral care products are in the form of lozenges or oral dispersible tablets.

The oral care products of the present invention may also comprise other orally active agents, such as teeth whitening actives, including bleaching or oxidizing agents like peroxides, perborates, percarbonates, peroxyacids, persulfates, metal chlorites, and combinations thereof. Teeth colour modifying substances may also be considered among the oral care actives useful in the present invention. The oral care products may additionally comprise flavouring compounds such as menthol.

The strains forming the composition of the invention are preferably in the form of viable cells. However, the strains of the invention can also be in the form of non-viable cells such as killed cultures or compositions containing beneficial factors produced by *Lactobacillus plantarum* CECT 7481 and *Lactobacillus brevis* CECT 7480. This could include thermally killed micro-organisms or micro-organisms killed by exposure to altered pH, sonication, radiation or subjection to pressure. With non-viable cells product preparation is simpler, cells may be incorporated easily into commercial products and storage requirements are much less limited than viable cells.

When used in the form of the composition of the invention, the strains can be in any concentration ratio suitable for the intended use. For instance, the strains can be in a concentration ratio which is comprised between of 3:1 and 1:3 (*Lactobacillus plantarum* CECT 7481: *Lactobacillus brevis* CECT 7480). Preferably the concentration ratio is 1:1. Further, the strains of the invention are included in the composition in an effective amount for the required use.

The term "effective amount" as used herein is the amount of colony forming units (cfu) for each strain in the composition that is high enough to significantly modify the condition to be treated in a positive way but low enough to avoid serious side effects (at a reasonable benefit/risk ratio), within the scope of sound medical judgment. An effective amount of said probiotic microorganism will be determined by the skilled in the art and will vary with the particular goal to be achieved, the age and physical condition of the patient being treated, the severity of the underlying disorder, and the final formulation. For instance, in oral health products, the strain or strains are present in an amount from about $10^5$ cfu/g to about $10^{12}$ cfu/g, preferably in an amount from about $10^7$ cfu/g to about $10^{11}$ cfu/g. The term "colony forming unit" ("cfu") is defined as number of bacterial cells as revealed by microbiological counts on agar plates. In a particular embodiment, the composition of the invention is an oral care product comprising between $10^7$-$10^{10}$ cfu/g.

Dietary supplements usually contain probiotic strains in an amount ranging from $10^5$ and $10^{12}$ cfu/g. In a particular embodiment, the composition of the invention is a dietary supplement comprising between $10^7$-$10^{10}$ cfu/g.

The strains of the invention are produced by cultivating the bacteria in a suitable medium and under suitable conditions. The strains can be cultivated alone to form a pure culture, or as a mixed culture together with other microorganisms, or by cultivating bacteria of different types separately and then combining them in the desired proportions. After cultivation, the cell suspension is recovered and used as such or treated in the desired manner, for instance, by concentrating or freeze-drying, to be further employed in the preparation of the products. Sometimes the probiotic preparation is subjected to an immobilisation or encapsulation process in order to improve the shelf life. Several techniques for immobilisation or encapsulation of bacteria are known in the art. In a particular embodiment, the strains forming part of the composition of the invention are incorporated to an oral care product as encapsulated bacteria.

As will be apparent to the skilled in the art, *Lactobacillus plantarum* CECT 7481 and *Lactobacillus brevis* CECT 7480 are effective not only when combined in a single composition, but also when used on their own, or in two different compositions administered simultaneously, sequentially or separately after a certain period of time. Furthermore, the person skilled in the art will understand that one of the strains can be prescribed to be used together with the other strain for oral health in order to prevent or treat oral disorders, particularly disorders that are produced by oral pathogens, more preferably dental-plaque related disorders and/or halitosis and/or candidiasis.

Consequently, one more aspect of the invention provides *Lactobacillus plantarum* CECT 7481.

Finally, another aspect of the invention provides *Lactobacillus brevis* CECT 7480.

The strains of the invention are described herein for the first time and are therefore new. As shown in FIG. 1, both strains, *Lactobacillus plantarum* CECT 7481 and *Lactobacillus brevis* CECT 7480, have a different pulsed field gel electrophoresis pattern than closely related commercial lactobacilli strains, such as *Lactobacillus plantarum* 299v, *Lactobacillus plantarum* VSL#3, *Lactobacillus casei* VSL#3 and *Lactobacillus casei* DN 114.001.

Some documents of the state of the art describe compositions comprising strains of *Lactobacillus plantarum* and *Lactobacillus brevis*. However, the composition of the invention is new with respect to said compositions.

In particular, KR100780030 discloses a fermented soy milk comprising strains of *Lactobacillus brevis* and *Lactobacillus plantarum*. The disclosed strains were isolated from kimchi, a meal consisting in fermented vegetables that is typical from Korea. In contrast, the strains of the invention were isolated from children saliva in a South American developing region, where kimchi is not consumed. Thus, the *L. brevis* and *L. plantarum* strains of the invention have a completely different origin, meaning that neither *Lactobacillus plantarum* CECT 7481 nor *Lactobacillus brevis* CECT 7480 are the same as the referred Korean strains.

Another Korean patent application, KR100866504, discloses a fermented red *ginseng* using *Lactobacillus plantarum* P2 (microbial deposition number KCTC11391BP) and/or *Lactobacillus brevis* M2 (microbial deposition number KCTC11390BP). These strains were isolated from *ginseng*. Again, the disclosed Korean strains have a completely different origin that the strains of the invention, since they were isolated from a plant that is not consumed in South American developing regions. This renders it impossible that either *Lactobacillus plantarum* CECT 7481 or *Lactobacillus brevis* CECT 7480 are the same as the referred Korean strains.

International patent applications WO2005/082157 and WO 02/39825, again disclose combinations of *L. plantarum* and *L. brevis* strains. The *L. brevis* LBRO1 strain disclosed in the composition of WO2005/082157 was isolated from mustard pickles in Taiwan. *L. brevis* C21 disclosed in the compositions of WO 02/39825 was isolated from Mongolian tofu. As above, according to the completely different origins of these *L. brevis* strains it is impossible for them to be the same as the strain of the present invention. Besides, the disclosed *L. brevis* LBRO1 and *L. brevis* C21 strains do not seem to be accessible to the public.

Further, WO 2006/080035 discloses a gynecological composition which contains *Lactobacillus brevis* CD2 and a non-specified *Lactobacillus plantarum* strain, along with a *L. salivarius* strain. However, strain *L. brevis* CD2 is different from *Lactobacillus brevis* CECT 7480. As shown in TABLE 4, when combining the strain *Lactobacillus plantarum* CECT 7481 with *L. brevis* CD2 an antagonistic effect is observed with respect to the ability to form aggregates. In contrast, the combination of *Lactobacillus plantarum* CECT with *Lactobacillus brevis* CECT 7480 results in a greater ability to form aggregates. Additionally, it has been demonstrated that *L. brevis* strain of the invention has a significantly lower acidification profile as compared with commercial *L. brevis* CD2 (see TABLE 5). Thus, *Lactobacillus brevis* CECT 7480 is not only different to *L. brevis* CD2, but also better suited for oral health applications. Altogether, while having different effects, the combination of the invention is different from that disclosed in WO 2006/080035.

Finally, WO 02/018542 mentions that *Lactobacillus* strains frequently found in cheddar cheese include *L. brevis* and *L. plantarum* strains and patent application FR2448865 (page 10, lines 11-17) discloses a composition containing *L. plantarum* to which *L. brevis* can be added. However, these documents do not disclose a composition containing a specific *L. brevis* strain and a specific *L. plantarum* strain. The composition of the invention comprising a specific *L. brevis* strain, namely *Lactobacillus brevis* CECT 7480, and a specific *L. plantarum* strain, namely, *Lactobacillus plantarum* CECT 7481 is therefore new.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided by way of illustration, and they are not intended to be limiting of the present invention.

BRIEF DESCRIPTION OF THE DRAWINGS

FIG. 1. Pulsed field electrophoresis patterns of Sfi-I (A, B) and Sma-I (C, D) restricted genomic DNA of: 1, *Lactobacillus plantarum* CECT 7481 (F2096); 2, *Lactobacillus plantarum* 299V; 3, *Lactobacillus plantarum* VSL#3; 4, *Lactobacillus brevis* CECT 7480 (I3141); 5, *Lactobacillus casei* VSL#3; 6, *Lactobacillus casei* DN 114.001. M stands for molecular marker.

EXAMPLES

The following sections describe the characterization of the strains of the invention and their specific probiotic features with regard to oral heath applications.
1. Isolation of Microorganisms Novel strains F2096 and I2141 were isolated from saliva from 0-5 year-old children from a tropical South American developing region. Saliva was dissolved in PBS buffer (pH 7.4), aliquoted and plated on MRS (Man Rogosa Sharp, Sigma-Aldrich Chem, Spain) agar supplemented with 10 µg/ml vancomycin (SIGMA). Strains were cultured under microaerophilic conditions (5% $CO_2$) at 37° C. Once grown, isolated strains were stored by lyophilisation in PBS 0.1× with 15% skim milk powder.

Strains F2096 and I3141 were identified as *Lactobacillus plantarum* and *Lactobacillus brevis*, respectively (see section 2 below). Both strains were deposited in the Spanish Type Culture Collection (Universitat de València, Campus de Burjassot, Edif. de Investigación, 46100 Burjassot, València, Spain). *Lactobacillus plantarum* (strain F2096) was deposited on 21 Jan. 2009 and given accession number 7481. *Lactobacillus brevis* (strain I3141) was deposited on 18 Feb. 2009 and given accession number 7480. Both deposited strains are viable and keep all their features related to their deposit.

As used hereinafter, strain F2096 corresponds to *Lactobacillus plantarum* CETC 7481, and strain I3141 to *Lactobacillus brevis* CECT 7480.

*Pediococcus acidilactici* F2019 (herein after referred to as *P. acidilactici*), *Lactobacillus paracasei* 13152 (herein after referred to as *L. paracasei*) and *Pediococcus pentosaceus* 154 (herein after referred to as *P. pentosaceus*) were isolated from human saliva as explained above. *Streptococcus salivarius* K12 was isolated from commercial BLIS K12® in TBS (tryptic soy broth) and cultured in aerobic conditions at 37° C. *Lactobacillus reuteri* ATCC 55730 strain was isolated from commercial Reuteri Drops®, *Lactobacillus plantarum* 299v from Poviva®, *Lactobacillus brevis* CD2 from Inersan®, *Lactobacillus plantarum* VSL#3 and *Lactobacillus casei* VSL#3 from VSL#3®, and *Lactobacillus casei* DN 114.001 from Actimel®. All of the latter strains were isolated on MRS, and cultured at 37° C. with 5% $CO_2$. Potentially pathogenic strains *Porphyromonas gingivalis* CIP 103683, *Fusobacterium nucleatum* CIP 104988, *Treponema denticola* CIP 103917 and *Prevotella denticola* CIP 104478T were obtained from Institut Pasteur, and cultured following provider's instructions. *Streptococcus mutans* of clinical origin was cultured on Brain Heart Agar at 37° C. and 5% $CO_2$. Identification of the strains was performed by sequencing.
2. Taxonomic Characterisation of Strains
2.1. Genus and Species Genetic Identification
A) Methods The strains of the invention were grown overnight on MRS medium (pH 6.4) at 37° C. in an atmosphere containing 5% $CO_2$. Bacteria were further harvested, washed and resuspended in pre-lysis buffer (480 µl EDTA 50 mM pH 8.0; 120 µl lysozyme 10 mg/ml), and further incubated at 37° C. for 60 min. DNA was extracted using Wizard genomic DNA purification kit (Promega). After centrifugation of the pre-treated bacteria at 14000 g for 2 min to remove the supernatant, the Promega's protocol was followed. In brief, bacteria were resuspended in Nuclei Lysis Solution and incubated at 80° C. for 5 min, then cooled to room temperature. Cell lysates were incubated in RNase solution at 37° C. for 60 min and proteins were precipitated by adding the Protein Precipitation Solution and vortexing at high speed. Samples were cooled down and centrifuged at 15000 g for 3 min. The supernatants containing the DNA were transferred to clean 1.5 ml microfuge tubes and mixed with 600 µl of isopropanol by inversion. DNA was collected by centrifugation at 15000 g for 2 min and carefully pouring off the supernatant. DNA samples were washed with 600 µl of 70% ethanol by gently inverting the tube several times. Ethanol was removed by aspiration, after centrifugation at 15000 g for 2 min. Finally, the DNA pellet was resuspended in 100 µl of Rehydration Solution by incubating at 65° C. for 1 h. Samples were stored at 2-8° C.

The 16S rRNA was amplified by PCR using the universal primers Eub27f and Eub1492r, which produce a fragment nearly full-sequence of 16S (more than 1000 nucleotides) (TABLE 1). Then, the DNA obtained as explained above was washed using the kit Quiaquick (Quiagene).

Four consecutive sequencing reactions were performed for each sample in a Genetic Analyzer 3130 (Applied Biosystems) using BigDye kit v.3.1, using the primers shown in TABLE 1. Data collection and chromatograms were built using DNA Sequence Analysis v.5.2 software (Applied Biosystems) and checked by visual analysis with Chromas (Technelysium Pty Ltd.) and BioEdit (Ibis Biosciences).

Genus Identification was carried out using the Ribosomal Database Project tool (Wang Q, et al., "Naive Bayesian Classifier for Rapid Assignment of rRNA Sequences into the New Bacterial Taxonomy", *Appl Environ Microbiol*, 2007, vol. 73, p. 5261-5267). Species identification was performed by comparison of the obtained sequence with 16S sequences of known organisms from both RefSeq data base (http://www.ncbi.nlm.nih.gov/RefSeq/) by means of a BLASTN, and from Ribosomal Database Project (http://rdp.cme.msu.edu/, J.R. Cole et al., "The Ribosomal Database Project (RDP-II): introducing myRDP space and quality controlled public data", Nucl. Acids Res., 2007, vol. 35, p. 169-172).

TABLE 1

Primers used for amplifying and sequencing the 16S gene

| Step | Primer | Orientation | 5' → 3' Sequence |
|---|---|---|---|
| Amplification | Eub27f | forward | GAGTTTGATCCTGGCTCAG (SEQ ID NO: 1) |
| | Eub1492r | reverse | TACGGYTACCTTGTTAC GACTT (SEQ ID NO: 2) |

TABLE 1-continued

Primers used for amplifying and
sequencing the 16S gene

| Step | Primer | Orientation | 5' → 3' Sequence |
|---|---|---|---|
| Sequencing | 27f | forward | AGAGTTTGATCCTGGCTCAG (SEQ ID NO: 3) |
| | 357f | forward | CGCCCGCCGCGCCCCGCGCC CGGCCCGCCGCCCCCGCCCC CCTACGGGAGGCAGCAG (SEQ ID NO: 4) |
| | 907r | reverse | CCGTCAATTCCTTTGAGTTT (SEQ ID NO: 5) |
| | 1492r | reverse | GGTTACCTTGTTACGACTT (SEQ ID NO: 6) |

B) Results

RDP (Ribosimal Database Project) tool identified strain F2096 as belonging to the *Lactobacillus plantarum* species and strain I3141 as belonging to *Lactobacillus plantarum* species.

2.2. Strain Genotyping

A) Methods

Characterization was performed by genomic digestion and pulsed-field gel electrophoresis. F2096 and I3141 strains were subjected to a previously described protocol (Rodas A M, et al. "Polyphasic study of wine *Lactobacillus* strains: taxonomic implications", *Int J Syst Evol Microbiol*, 2005, vol. 55, p. 197-207). Commercial strains, *Lactobacillus plantarum* 299V, *Lactobacillus plantarum* VSL#3, *Lactobacillus casei* VSL#3 and *Lactobacillus casei* DN 114.001 were also included in the assay as control strains. All strains were grown on MRS agar plates and incubated at 37° C., 5% $CO_2$ for 18 h. Cells were harvested and washed 3 times in 8 ml PET (10 mM Tris pH 7.6, 1 M NaCl), then centrifuged at 6000 rpm 10 min. Pellets were resuspended in 700 µl lysis buffer (6 mM Tris, 1 M NaCl, 0.1 M EDTA, 0.5% SLS, 0.2% deoxycholic acid; 1 mg/ml lysozyme; 40 U/ml mutanolysin; 20 (g/ml RNase). An equal volume of 1.6% low melting point agarose (FMC Bio-Products, Rockland, Me., USA) was added to the resuspended cells and solidification was allowed at 4° C. for 1 h. Inserts were transferred to 2 ml lysis buffer II (0.5 M EDTA pH 9.2, 1% N-lauryl sarcosine and 1 mg/ml pronase) and incubated at 50° C. for 48 h. Then inserts were washed at room temperature with TE buffer (10 mM Tris, 1 mM EDTA pH 8.0). Total DNA digestion was performed by Sfi-I and Sma-I restriction enzymes (Roche Diagnostics).

Pulse-field electrophoresis was carried out using CHEF DRIII apparatus (BioRad Laboratories). Inserts were loaded in a 1% agarose gel (SeaKem ME agarose, FMC BioProducts, ME, USA). TABLE 2 describes electrophoresis conditions for each enzyme. DNA molecular weight markers were Lambda ladder PFG Marker and Low Range PFG Marker (New England Biolabs). After electrophoresis, gels were stained with ethidium bromide and UV using GelDoc System (BioRad).

TABLE 2

Electrophoresis conditions for Sfi-I and Sma-I restricted genomic DNA from F2096 and I3141 strains.

| Enzyme | Block | Initial Pulse (sec) | Final Pulse (sec) | Time (hours) |
|---|---|---|---|---|
| Sfi-I | 1 | 2 | 10 | 10 |
| | 2 | 15 | 25 | 6 |
| Sma-I | 1 | 0.5 | 5 | 16 |

B) Results

As shown in FIG. 1, pulsed field electrophoresis Sfi-I and Sma-I restriction patterns for F2096 strain differed with those for the commercial *Lactobacillus plantarum* 299v and *Lactobacillus plantarum* VSL#3 strains, while restriction patterns for I3141 differed from those of the closely related commercial *Lactobacillus casei* strains. Thus, it may be concluded that F2096 and I3141 strains are new strains.

3. Ability to Antagonize Pathogens

A) Methods

In order to asses whether strains F2096 and I3141 presented antagonistic activities, a Campbell protocol was performed using agar plates seeded with bacterial pathogens in Oxoid medium. Pathogens used in this study were selected among those commonly present in the human oral cavity (see TABLE 1). Briefly, F2096, I3141 and *P. acidilactici*, another strain isolated from human saliva, were cultured overnight, each at the specific conditions mentioned above. After incubation, cultures were standardised to $10^8$ cfu/ml and the following mixed cultures were prepared: F2096+I3141, F2096+ *P. acidilactici*, and I3141+*P. acidilactici*. Said mixed cultures contained an equal amount of each of their constituent strains and the same total bacterial concentration as the single-strained cultures, i.e. $10^8$ cfu/ml. A fixed volume of each of the single-strain cultures and mixed cultures was plated uniformly and grown to confluence at the appropriate temperatures in a 5% $CO_2$ incubator. Then, uniformly sized cylinder sections of confluent agar plates were placed loan-to-loan over the pathogen plate and incubated overnight at 37° C.

Next day, inhibition zones were measured by placing the agar plate over a flat rule. Antagonistic properties of the strains were measured as growth inhibitory activity (GIA), which was calculated by subtracting the cylinder diameter (CD) from the inhibition zone diameter (IZD) and dividing this difference by two following the formula GIA=(IZD-CD)/2. The inhibiting capabilities of the strains of this invention were compared to that of the commercial oral probiotic strains *Streptococcus salivarius* K12 and *Lactobacillus reuteri* ATCC 55730.

B) Results

The growth inhibitory activities of the strains F2096 and I3141 are shown in

TABLE 3

Growth inhibitory activity against oral pathogens

| | P. gingivalis | F. nucleatum | T. denticola | P. denticola | S. mutans | F2096 | I3141 |
|---|---|---|---|---|---|---|---|
| F2096 | 1 | 4 | 4.5 | NI | 2 | — | NI |
| I3141 | NI | 7 | 1 | 0.5 | 2 | NI | — |
| F2096 + I3141 | 1.5 | 9 | 4.5 | 1 | 4 | — | — |
| F2096 + P. acidilactici | 0.5 | 1 | 4 | NI | 1 | — | — |

TABLE 3-continued

Growth inhibitory activity against oral pathogens

| | P. gingivalis | F. nucleatum | T. denticola | P. denticola | S. mutans | F2096 | I3141 |
|---|---|---|---|---|---|---|---|
| I3141 + P. acidilactici | NI | 5 | 0.5 | NI | NI | — | — |
| S. salivarius | NI | NI | 1 | 0.5 | 1 | — | — |
| L. reuteri | NI | 0.5 | NI | 0.75 | 1 | — | — |

NI, no inhibition

As can be seen by the present results, both P2096 and I3141 have a broad inhibition pattern against oral pathogens. This is especially relevant for *P. gingivalis*, since a preliminary study showed that antagonistic activity against this pathogen is rare (results not shown). Further, it is noteworthy that the combination of F2096 and I3141 in a mixed culture displays a higher antagonistic activity against oral pathogens as compared to the activity of the individual strains used separately as single cultures—it is to note that the concentration of each strain in the mixed culture is half of that in the single cultures, therefore the antagonistic effect of the combination is higher than the sum of the individual effects for these strains-. This synergistic effect does not occur when each of the strains were combined with another inhabitant of the oral cavity, *P. acidilactici*. Thus, the strains of the invention display a synergistic activity against oral pathogens and are especially useful when used in a single formula.

When compared with commercial probiotics *Streptococcus salivarius* K12 and *Lactobacillus reuteri* ATCC 55730, the strains of the invention have a significantly higher antagonistic capacity. Finally, F2096 and I3141 displayed minimal antagonism against each other or common commensal strains of the human oral flora.

4. Formation of Aggregates

A) Methods

The ability to form aggregates was evaluated by monitoring the diminution of the optical density at 620 nm of overnight cultures due to formation of aggregates and precipitation. Percent aggregation capacity (% AC) value was obtained using the following formula: % $AC=(1-(OD_{tf}/OD_{t0})/100$, where $OD_{tf}$ and $OD_{t0}$ are the optical density at final and initial times, respectively. OD at initial times was adjusted so that all cultures contained an equivalent number of cfu/ml. Combined cultures were prepared by mixing an appropriate amount of single strains as to obtain the desired total cfu/ml containing 50% of each strain.

B) Results

The ability to form aggregates is important for a probiotic strains with oral health applications because it enables said strains to inhibit or reduce dental plaque by interfering with pathogens biofilm formation.

Mean aggregation capacity values for the new strains and their combination among them or with *P. acidilactici* or *L. brevis* CD2 are shown in TABLE 4 as compared to control strains. These results clearly demonstrate that the new isolates showed very good aggregation activity, significantly higher than both commercial controls *S. salivarius* K12 and *L. reuteri* ATTC 55730. Further, aggregate formation by the strains of the invention is increased when both strains are combined in a mixed culture, meaning that the strains are more effective in displacing pathogenic bacteria when combined into a single composition. This cooperation is, however, not present when the strains of the invention are separately combined with other strains with good aggregation capacity, such as *P. acidilactici* and *L. brevis* CD2. Moreover, when combining the strains of the invention with *L. brevis* CD2, an antagonistic effect is observed, meaning that the strains of the invention are less effective in displacing pathogenic bacteria when combined with *L. brevis* CD2.

TABLE 4

Aggregation capacity (%)

| STRAIN | Aggregation capacity (%) |
|---|---|
| F2096 | 56.00 |
| I3141 | 22.73 |
| F2096 + I3141 | 64.73 |
| F2096 + P. acidilactici | 55.50 |
| I3141 + P. acidilactici | 23.30 |
| L. brevis CD2 | 24.70 |
| F2096 + L. brevis CD2 | 36.31 |
| I3141 + L. brevis CD2 | 28.50 |
| S. salivarius | 16.67 |
| L. reuteri | 0.00 |

5. Production of Acid

A) Methods

The ability of the new strains to produce acid when growing in culture media supplemented with different sugars present in human diet was evaluated. The strains were grown during 18 h at 37° C. and 5% $CO_2$ in the following media: MRS and minimal medium supplemented with 4% glucose, 4% fructose, 4% lactose or 4% sucrose. Minimal medium contained 2 g/L peptone water, 2 g/L yeast extract, 0.1 g/L NaCl, 0.04 g/L $K_2HPO_4$, 0.04 g/L $KH_2PO_4$, 0.01 g/L $MgSO_4*7H_2O$, 0.01 g/L $CaCl_2*6H_2O$, 2 g/L $NaHCO_3$, 0.05 g/L hemina (dissolved in a few 1 mol/L NaOH drops), 0.5 g/L cysteine HCl, 0.5 g/L bile salts, 2 g/L Tween 80, and 10 μl vitamin K1 (all components obtained from Sigma-Aldrich Chem, Spain). Cultures were adjusted at pH 7 with HCl. The pH and the number of viable cells (cfu/ml) were measured at the end of the incubation time. Production of acid value for each culture medium was obtained by the following formula: PA value=pH*log (cfu/ml).

B) Results

According to the formula depicted above, low values correspond to highly acidogenic strains. High acid production is an undesirable side effect for oral probiotics, since it promotes caries formation. The acid production value for F2096 and I3141 and several probiotic control strains grown on different sugars can be seen in TABLE 5, together with the values obtained for commercial strains. MM stands for minimal medium.

TABLE 5

Production of acid

| strain | MRS | MM + Gluc | MM + Fruc | MM + Lac | MM + Sac |
|---|---|---|---|---|---|
| F2096 | 32.7 | 30.34 | 28.56 | 31.45 | 31.67 |
| I3141 | 42.04 | 48.28 | 45.24 | 58.24 | 59.12 |
| L. brevis CD2 | 26.45 | 31.24 | 24.24 | 21.45 | 24.20 |
| S. salivarius | 41.37 | 29.69 | 31.31 | 28.03 | 29.85 |
| L. reuteri | 36.75 | 49.19 | 45.67 | 34.01 | 57.39 |
| L. paracasei | 27.38 | 19.53 | 8.21 | 5.98 | 20.52 |
| P. pentosaceus | 24.7 | 11.34 | 13.23 | 12.56 | 17.45 |
| P. acidilactici | 22.6 | 15.61 | 11.10 | 16.45 | 22.14 |

These results demonstrate that growth of strains F2096 and I3141 in different sugars results in a remarkably poor acid production as compared with other bacterial strains that had also been isolated from the oral cavity, namely, L. paracasei, P. pentosaceus and P. acidilactici. The strains of the invention are also less acidogenic than commercial oral probiotic S. salivarius K12. Additionally, strain I3141 has a lower acidification profile when compared to L. reuteri ATTC 55730, which is known to be particularly low acidogenic and is being marketed as an anti-cariogenic probiotic. It is also noteworthy that L. brevis strain of the invention I3141 has a significantly lower acidification profile as compared with commercial L. brevis CD2. Therefore, strains F2096 and I3141 have a low acidification profile, thus being suitable for oral health applications.

6. Production of Malodor Volatile Compounds

A) Methods

The production of malodor volatile compounds by the new strains was determined when growing in a culture medium resembling human diet by means of a sensorial evaluation. Briefly, strains were grown in the medium which contains glucose (0.5% w/v), fructose (0.5% w/v), yeast extract (1% w/v), meat extract (1% w/v), eukaryotic cells (200 cells/ml) and pectin (0.5% w/v) during 48 h at 37° C. and 5% CO2. The strains receive a production of malodor value between 1 and 5, where 1 is absence of odor and 5 is a very unpleasant odor.

B) Results

The production of malodor compounds is very undesirable for an oral probiotic. However, the strains of the invention produced no unpleasant odors whatsoever while growing in a culture medium that resembled human diet.

TABLE 6

Production of unpleasant odors

| Strain | Malodor value |
|---|---|
| F2096 | 2 |
| I3141 | 2 |
| S. salivarius | 2 |
| L. reuteri | 3 |

7. Survival to Oral Conditions

A) Methods

Survival of the strains in the oral cavity was studied by subjecting them to oral stress conditions. $5*10^7$ cfu of each bacterial strain was inoculated in 96-well culture plates on 200 μl of MRS medium, in the case of F2096, I3141 and L. reuteri ATCC 55730, or Tryptic Soy Broth (TSB, Oxoid) in the case of S. salivarius K12. Cultures were supplemented with physiological concentrations of lysozyme (Sigma-Aldrich Chem, Spain) or hydrogen peroxide (Sigma-Aldrich Chem, Spain). Plates were incubated at 37° C. and 5% $CO_2$ for six hours. Bacterial growth was quantified by measuring optical density at 620 nm. Bacterial growth value was obtained by comparison with the growth achieved by the same strain in standard MRS medium without supplements.

B) Results

A percentage global survival value (% SV) was calculated as follows: % SV=[$(OD_{tf}-OD_{t0}$ (with supplement))/$(OD_{tf}-OD_{t0}$ (without supplement))]*100, where OD is optical density, and tf and t0 are final time and initial time, respectively. The following values are the average of triplicate results:

TABLE 7

Survival to oral conditions

| Strain | MRS/TSB Lisozyme $2 \times 10^5$ U/ml | MRS/TSB $H_2O_2$ 1 mM | MRS/TSB $H_2O_2$ 2,5 mM |
|---|---|---|---|
| F2096 | 44.41 | 98.78 | 62.60 |
| I3141 | 0.58 | 42.06 | 84.28 |
| S. salivarius | 0.50 | 18.89 | 28.78 |
| L. reuteri | −17.46 | 31.32 | −8.03 |

New strains F2096 and I3141 showed better resistance to oral stress than commercial strains S. salivarius K12 and L. reuteri ATCC 55730.

8. Ability to Adhere to Oral Tissues

A) Methods

In vitro adhesion assay of F2096, I3141, and commercial control strains to intestinal pig tongue, Caco-2 cells (to simulate gum) and hydroxyapatite (HA) beads (to simulate teeth) were carried out. Each strain was incubated overnight with 10 μl/ml 5-[3H]thymidine (1.0 μCi/ml, Amersham Biosciences, UK). The preparations were centrifuged and pellets re-suspended in PBS buffer to a concentration of $10^8$ cfu/ml. The tritium signal incorporated to the microorganisms is calculated from the initial tritium signal and the supernatant signal in a scintillation reader (Wallac 1410). The ratio between this number (signal incorporated to the biomass) and the total number of microorganisms in the culture results in cpm/cfu (signal/bacterium).

The adhesion measurement was performed by the addition of 3.3 ml of radio-labeled-$10^8$ cfu of each strain to either 1.05*0.5 cm-fragments of pig tongue or pre-incubated Caco-2 cells or 50 mg of HA beads (80 μm of diameter) in ELISA plates. After 45 min, supernatants were carefully removed. HA beads (together with adhered bacteria) were recovered by centrifugation. The tongue or Caco-2 cells together with the adhering bacteria were scrapped from the ELISA wells. Finally, recovered bacteria were lysed to calculate specific radioactivity (cpm/cfu).

All assays were performed in triplicate and results expressed as the number of bacteria adhered per $cm^2$. Since S. salivarius displayed better results for most researched properties (see above results), this strain was used as control strain for the adhesion assay.

B) Results

TABLE 8

Adhesion to oral tissues

| Strain | tongue (cfu/cm²) | Caco-2 (cfu/cm²) | HA beads (cfu/cm²) |
|---|---|---|---|
| F2096 | 8.84E+06 | 1.00E+06 | 2.30E+06 |
| I3141 | 2.70E+06 | 3.78E+04 | 5.51E+05 |
| S. salivarius | 1.72E+06 | 8.83E+04 | 2.34E+05 |

These results demonstrate that strains F2096 and I3141 have global better adhesion capacity to oral tissue when compared with oral probiotic strain *S. salivarius* K12. The ability to adhere to oral tissues is a relevant feature for strains to be used as probiotics since it gives these bacteria a competitive advantage when competing for adhesion sites against pathogens and favoring permanence in the oral cavity. As a result, strains that display good adhesion to oral tissues contribute to displace pathogens from the oral cavity and promote a healthier oral flora.

9. Antibiotic Susceptibility

A) Methods

Antibiotic susceptibility for strains F2096 and I2141 was studied following the technical guidance given by the European Food Safety Authority (EFSA) ("Update of the criteria used in the assessment of bacterial resistance to antibiotics of human or veterinary importance". The EFSA Journal, 2008, vol. 732, p. 1-15). Culture conditions for the strains were as follows: growth on surface of MRS agar plates containing EFSA recommended antibiotic concentrations at 37° C. and 5% $CO_2$.

B) Results

Growth of the strains on antibiotic-containing media is presented on TABLE 9. Concentrations for each antibiotic to be assayed as recommended by EFSA are given in mg/ml. No indicated values for antibiotic concentrations are specified by EFSA for *L. brevis* species, therefore, antibiotic resistance in *L. brevis* strain I3141 was assayed using the concentrations recommended for obligate heterofermentative lactobacilli, to which group this species belongs.

Results indicate that F2096 and I2141 present no antibiotic resistance. They are therefore suitable for human consumption.

TABLE 9

Antibiotic resistance of strains F2096 and I3141.

| | EFSA concentration for *L. plantarum* | Growth of F2096 | EFSA concentration for obligate heterofermentative lactobacilli | Growth of I3141 |
|---|---|---|---|---|
| Ampicillin | 2 | none | 2 | none |
| Gentamycin | 16 | none | 16 | none |
| Kanamycin | 64 | none | 16 | none |
| Streptomycin | n.r. | none | 64 | none |
| Erythromycin | 1 | none | 1 | none |
| Clindamycin | 1 | none | 1 | none |
| Quinuspristin/ Dalfopristin | 4 | none | 4 | none |
| Tetracyclin | 32 | none | 8 | none |
| chloramphenicol | 8 | none | 4 | none | n.r., not recommended by EFSA

BIBLIOGRAPHIC REFERENCES

Twetman S, et al. "Short-term effect of chewing gums containing probiotic *Lactobacillus reuteri* on the levels of inflammatory mediators in gingival crevicular fluid". *Acta Odontol Scand*, 2009, vol. 67, p. 19-24.

Caglar E, et al. "Salivary *mutans* streptococci and lactobacilli levels after ingestion of the probiotic bacterium *Lactobacillus_reuteri* ATCC 55730 by straws or tablets". *Acta Odontol Scand*, 2009, vol. 64, p. 314-318.

Stamatova I, et al. "In vitro evaluation of yoghurt starter lactobacilli and *Lactobacillus rhamnosus* GG adhesion to saliva-coated surfaces". *Oral Microbiol Immunol*, 2009, vol. 24, p. 218-223.

Burton J P, et al. "Preliminary study of the effect of probiotic *Streptococcus salivarius* K12 on oral malodor parameters". *J Appl Microbiol*, 2006, vol. 100, p. 754-764.

Wang Q, et al., "Naive Bayesian Classifier for Rapid Assignment of rRNA Sequences into the New Bacterial Taxonomy", *Appl Environ Microbiol*, 2007, vol. 73, p. 5261-5267.

Ribosomal Database Project: <http://rdp.cme.msu.edu/>

J R Cole et al., "The Ribosomal Database Project (RDP-II): introducing myRDP space and quality controlled public data", Nucl. Acids Res., 2007, vol. 35, p. 169-172.

Rodas A M, et al. "Polyphasic study of wine *Lactobacillus* strains: taxonomic implications", *Int J Syst Evol Microbiol*, 2005, vol. 55, p. 197-207.

"Update of the criteria used in the assessment of bacterial resistance to antibiotics of human or veterinary importance". The EFSA Journal, 2008, vol. 732, p. 1-15.

The invention claimed is:

1. A method for the prevention and/or treatment of a disorder caused by oral pathogenesis in an oral cavity of a subject, comprising administering to the subject a composition comprising an effective amount of the isolated strain of *Lactobacillus plantarum* deposited in the Spanish Type Culture Collection (CECT) under accession number CECT 7481.

2. The method of claim 1, wherein the composition further comprises an effective amount of the isolated strain of *Lactobacillus brevis* deposited in the Spanish Type Culture Collection (CECT) under accession number CECT 7480.

3. The method of claim 1, wherein the disorder of the oral cavity is a dental plaque-related disorder.

4. The method according to claim 3, wherein the dental plaque-related disorder is gingivitis, periodontitis, carries, or sensitive teeth.

5. The method according to claim 1, wherein the disorder of the oral cavity is halitosis.

6. The method according to claim 1, wherein the disorder of the oral cavity is candidiasis.

7. A method for the prevention and/or treatment of a disorder caused by oral pathogenesis in an oral cavity of a subject, comprising administering to the subject a composition comprising an effective amount of *Lactobacillus brevis* deposited in the Spanish Type Culture Collection (CECT) under accession number CECT 7480.

8. The method of claim 7, wherein the composition further comprises an effective amount of the isolated strain of the isolated strain of *Lactobacillus plantarum* deposited in the Spanish Type Culture Collection (CECT) under accession number CECT 7481.

9. The method of claim 7, wherein the disorder of the oral cavity is a dental plaque-related disorder.

10. The method according to claim 9, wherein the dental plaque-related disorder is gingivitis, periodontitis, carries, or sensitive teeth.

11. The method according to claim 7, wherein the disorder of the oral cavity is halitosis.

12. The method according to claim 7, wherein the disorder of the oral cavity is candidiasis.

13. A method for the prevention and/or treatment of a disorder caused by oral pathogenesis in an oral cavity of a subject, comprising administering to the subject an effective amount of a composition comprising:

(a) the isolated strain of *Lactobacillus plantarum* deposited in the Spanish Type Culture Collection (CECT) under accession number CECT 7481; and
(b) the isolated strain of *Lactobacillus brevis* deposited in the Spanish Type Culture Collection (CECT) under accession number CECT 7480.

14. The method of claim 13, wherein the disorder of the oral cavity is a dental plaque-related disorder.

15. The method according to claim 14, wherein the dental plaque-related disorder is gingivitis, periodontitis, carries, or sensitive teeth.

16. The method according to claim 13, wherein the disorder of the oral cavity is halitosis.

17. The method according to claim 13, wherein the disorder of the oral cavity is candidiasis.

* * * * *